US006616950B2

(12) United States Patent
Pushpangadan et al.

(10) Patent No.: US 6,616,950 B2
(45) Date of Patent: Sep. 9, 2003

(54) FERMENTED HERBAL HEALTH DRINK FROM PLANT *ANDROGRAPHIS*

(75) Inventors: Palpu Pushpangadan, Lucknow (IN); Shanta Mehrotra, Lucknow (IN); Ajay Kumar Singh Rawat, Lucknow (IN); Sayyada Khatoon, Lucknow (IN); Sharad Kumar Srivastava, Lucknow (IN); Subha Rastogi, Lucknow (IN); Manjoosha Chaubay, Lucknow (IN); Adarsh Kumar Agnihotri, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/043,176

(22) Filed: Jan. 14, 2002

(65) Prior Publication Data

US 2003/0138509 A1 Jul. 24, 2003

(51) Int. Cl.$^7$ .............................................. A61K 35/78
(52) U.S. Cl. ........................ 424/725; 424/736; 424/777
(58) Field of Search ................................ 424/725, 736, 424/777

(56) References Cited

U.S. PATENT DOCUMENTS 6,136,316 A * 10/2000 Mehrotra et al.

* cited by examiner

*Primary Examiner*—Francisco Prats
*Assistant Examiner*—Susan D Coe
(74) *Attorney, Agent, or Firm*—Birch, Stewart, Kolasch & Birch, LLP

(57) ABSTRACT

The present invention relates to a fermented herbal health drink, comprising extract from plant Andrographis, extract from barley, wheat, and/or fruit and ethanol concentration ranging between 3 to 13% in the total health drink and optionally extract from plant Tinospora and other additives, said drink not containing hops and still having characteristic taste of a beer with no adverse effect and contributing to several medicinal properties comprising anti-oxidant, nervine relaxant, cholerectic, cardio-tonic, diurectic, digestive and immunomodulant, and a method of producing the herbal health drink, preferably a method of introducing bitterness into said health drink and using the same as a beer or to produce beer with said medicinal properties.

69 Claims, No Drawings

FERMENTED HERBAL HEALTH DRINK FROM PLANT ANDROGRAPHIS

FIELD OF THE PRESENT INVENTION

The present invention relates to a fermented herbal health drink, comprising extract from plant Andrographis, extract from barley, wheat, and/or fruit and ethanol concentration ranging between 3 to 13% in the total health drink and optionally extract from plant Tinospora and other additives, said drink not containing hops and still having characteristic taste of a beer with no adverse effect and contributing to several medicinal properties comprising anti-oxidant, nervine relaxant, cholerectic, cardio-tonic, diurectic, digestive and immunomodulant, and a method of producing the herbal health drink, preferably a method of introducing bitterness into said health drink and using the same as a beer or to produce beer with said medicinal properties.

BACKGROUND AND PRIOR ART REFERENCES OF THE PRESENT INVENTION

Beer is an alcoholic beverage made from malted grains, hops, yeast and water. Fruit, herbs and spices are also used for flavors.

In the distant past, the term beer and 'ale' meant different things—'Ale' referred to drink without using hops while 'beer' with hops. Since virtually all commercial products now use hops, obtained from the female strobiles of *Himulus lupulus*, a temperate growing plant, and cultivated in England, Germany, Belgium, France, Russia and California.

In India it can be grown only in high attitude of Kashmir and Himalayas. The inventors undertook a critical study of wildly growing Indian medicinal plants, which are bitter in taste and can be a substitute of hops in alcoholic beverages, preferably in beer.

Reference is made to website (http://www.botanical.com/botanical/mgmh/h/hops-32.html) wherein, recipes for herb beers like Dandelion, Nettle, Meadow, Sweet, Yarrow hop and bitters are given. Hop Bitters are mentioned as appetizer and the Nettle Beer is often given as a remedy for gouty and rheumatic pains as shown in a website (http://www.botanical.com/botanical/mgmh/n/nettle.03.html).

Another reference is made to website http://www.foodnavigator.com-news letter, dated 2.1.2001 wherein Riva Brewery of Dentegem, Belgium brewed fruity beers with cherries and strawberries.

Yet another reference is made to the Soma Products Co. at www.somaherbal.com wherein, 'Soma herbal'—a non-alcoholic herbal beer containing only 70 calories per bottle have been marketed by Soma Products Co. (Cherry Hill-N.J.). SOMA is a precise blend of herbs. Scullcap, Passion Flower, St. John's Wort and Kava Kava and the herbal formulation is designed to make the consumer feel relaxed and satisfied with a healthy herbal high or "huzz".

Still another reference is made to the website (http://www.winxwired.com/4point3/bp43.html) wherein the flavored beers are developed from oysters, carrots, peppermint, strawberry, rasberry, cherry and other fruits. Another 'medicinal herbal beer' has been developed by bog myrtle, yellow and marsh rosemary in place of hops.

Reference is made to Stephen Beaumont (1999) who tested a new beer flavored with fresh oranges prepared by Craftsman, Brewing Company, California.

Reference is made to website http://www.sallys-place.com/beverages/ber wherein Sara Doersam, a beer judge, described the history of beer brewing. Wheat beer, Vintage beer, Oktoberfest, real Ale, Red beer, Sake, Stout beer, Belgian beers etc. and her ten favorite beers. Almost all beers contain either hops for bitterness or hop flavor.

Another reference is made to the website http://www.foodnavigator.com/ingredients2 wherein a concentrated beer is described. It is prepared by spray drying beer with maltodrestrin, which removes water and alcohol, concentrating the flavor of beer in a free flowing powder.

Reference is made to a patent number JP2000060486 wherein, a food and drink showing hypercholesteremia improving action and anti-inflammatory action contain *Tinospora tuberculata* powder or its extract in a ratio of 1–7%. The other properties like antioxidant, immuno-enhancing, anti-fatigue, antiaging and hepatoprotective are not found in this drink and it is also not reported as a alternative source of hops for bitterness in beer.

Reference is made to website http//www.mediket2000.com/alternativemedi/ayurvedtherapy Wherein, *Tinospora cordifolia* (*guduchi*) is mentioned as an alternative medicine of ayurveda. It is reported as a good tonic to help build up new tissues, increases longevity, helps in rejuvenation of body, and also helps relieves stress and strain.

Reference is made to a website www.ayurvedhealthcare.com, wherein *Tinospora cordfolia* is mentioned as antioxidant, immunomodulator, hypoglycemic, analgesic, tonic, antipyretic, anti-arthritic, anti-inflammatory, anti-allergic and anti-stress, are also reported as beneficial in AIDS.

Reference is also made to website http://www.realbeer.com/spencer/ wherein a detailed description of beer prepared by hops is given.

Reference is made of (http://www.geocities.com/heartland/prairie/3490/herbal-rem.html) wherein the medicinal properties of beer like sedative, stomach soothing, diuretic, appetite, stimulating and as a relieving agent in nervine spasm. The properties like antioxidant, immuno-enhancing, anti-aging, anti-fatigue and hepatoprotective and are not found in hops.

Diet or food therapy is emerging as the latest trend in health care programme. It is now believed that there will be more dieticians than physicians will in the present century, as many diseases can be prevented if the right kind of diet is prescribed. Consumption of the right kind of food articles and drinks suited to the climate, age and constitution. Nature of the individuals are getting greater scientific, with high stress on health protection. The rich and traditional diet practice is prevalent among various communities with the regional variations, which are now found to be health protective/promotive. Over 1000 different kinds of alcoholic drinks, soft drinks, beverages and medicinal drinks are traditionally consumed in India. But unfortunately, with the introduction of various exotic drinks, many of the local drinks, which are mostly plant based, are fast disappearing and some of them are totally forgotten.

OBJECTIVES OF THE PRESENT INVENTION

The main object of the present invention is to develop herbal health drink.

Another object of the present invention is to develop fruit based herbal health drink.

Yet another object of the present invention is to develop herbal health drink using plant Andrographis.

Still another object of the present invention is to develop herbal health drink using plant Andrographis in combination with plant Tinospora.

Still another object of the present invention is to develop herbal health drink with medicinal properties.

Still another object of the present invention is to develop herbal health drink with taste of a beer.

Still another object of the present invention is to develop method to produce herbal health drink having medicinal properties.

Still another object of the present invention is to develop method to introduce bitterness into herbal health drink.

Still another object of the present invention is to prepare herbal beer with Andrographis replacing hops for bitterness in the same.

SUMMARY OF THE PRESENT INVENTION

The present invention relates to a fermented herbal health drink, comprising extract from plant Andrographis, extract from barley, wheat, and/or fruit and ethanol concentration ranging between 3 to 13% in the total health drink and optionally extract from plant Tinospora and other additives, said drink not containing hops and still having characteristic taste of a beer with no adverse effect and contributing to several medicinal properties comprising anti-oxidant, nervine relaxant, cholerectic, cardio-tonic, diurectic, digestive and immunomodulant, and a method of producing the herbal health drink, preferably a method of introducing bitterness into said health drink and using the same as a beer or to produce beer with said medicinal properties.

DETAILED DESCRIPTION OF THE PRESENT INVENTION

Accordingly the present invention relates to a fermented fruit based herbal health drink useful as an antioxidant, cardio-tonic, diuretic, digestive, choleretic, nervine relaxant and immunomodulant, comprising extract from plant Andrographis with concentration ranging between 0.5 to 10%, extract from fruit, and ethanol ranging between 3 to 13% in the total herbal health drink, optionally extract from plant Tinospora and other additives.

In an embodiment of the present invention additives are selected from a group comprising coloring agents, sugar, carbonated water, and preservatives.

In another embodiment of the present invention wherein, fermentation enhancers are selected from a group comprising grains of wheat and barley.

In yet another embodiment of the present invention wherein, fruits are selected from a group comprising *Mangifera indica, Phyllanthus emblica, Psidium guajava,* and *Citrus* spp.

In still another embodiment of the present invention wherein, said health drink obtained by combination of extract from plants Andrographis and Tinospora is superior to the one obtained from the plant Tinospora or Andrographis alone.

In still another embodiment of the present invention, the plant extract is obtained in aqueous medium or organic medium. The natures of medium do not affect the properties of the said drink.

In still another embodiment of the present invention has extract of plants Andrographis and Tinospora in the ratio ranging between 25:1 to 1:150.

In still another embodiment of the present invention wherein, fermentation enhancer is mixed with the fruit extract at the concentration ranging between 10 to 20%.

In still another embodiment of the present invention can be freshly prepared throughout the year.

In still another embodiment of the present invention wherein, plant extract is mixed with the fruit base material at the concentration ranging between 0.5 to 2%.

In still another embodiment of the present invention wherein, sugar is added to fruit extract in the ratio ranging between 1:3 and 2:5.

In still another embodiment of the present invention wherein, carbonated water is added to stock herbal drink in the ratio ranging between 1:3 to 2:5 to get herbal drink.

In still another embodiment of the present invention has bitterness value ranging between 175 to 210.

In still another embodiment of the present invention wherein, all the vegetative part of the said plants contributes to bitterness.

In still another embodiment of the present invention has alcohol content ranging between 2 to 8%.

In still another embodiment of the present invention has aroma.

In still another embodiment of the present invention has refreshing property.

In still another embodiment of the present invention has an ability to quench thirst.

In still another embodiment of the present invention provides instant energy.

In still another embodiment of the present invention fight fatigue.

In still another embodiment of the present invention the drink is a safe health protective and preventive drink.

In still another embodiment of the present invention wherein, medicinal properties of said plant extract is not affected by the presence of other constituents of the said drink.

In an embodiment of the present invention a method of producing a fermented fruit based herbal health drink useful as an antioxidant, cardio-tonic, diuretic, digestive, choleretic, nervine relaxant and immunomodulant, comprising extract from plant Andrographis with concentration ranging between 0.5 to 10%, extract from fruit, and ethanol ranging between 3 to 13% in the total herbal health drink, optionally extract from plant Tinospora and other additives.

In another embodiment of the present invention obtaining aqueous extract from said plant, In yet another embodiment of the present invention concentrating the aqueous extract, In still another embodiment of the present invention lyophilizing the concentrated extract, In still another embodiment of the present invention crushing said fruit extract, In still another embodiment of the present invention adding sugar to crushed fruit extract, In still another embodiment of the present invention obtaining fruit base material, In still another embodiment of the present invention autoclaving the said base material, In still another embodiment of the present invention mixing fermentation enhancer and lyophilized extract with base material, In still another embodiment of the present invention adding mixture with said inoculum for fermentation, in aseptic conditions, In still another embodiment of the present invention fermenting mixture for 4 to 10 days, In still another embodiment of the present invention filtering the fermented material, In still another embodiment of the present invention pasteurizing the filtrate, In still another embodiment of the present invention obtaining stock herbal drink, In still another embodiment of the present invention adding carbonated water to stock herbal drink, In still another embodiment of the present invention obtaining fruit based fermented health drink, and In still another embodiment of the present invention adding preservatives and coloring agents to drink.

In still another embodiment of the present invention wherein, additives are selected from a group comprising coloring agents, and preservatives.

In still another embodiment of the present invention wherein, fermentation enhancers are selected from a group comprising grains of wheat and barley.

In still another embodiment of the present invention wherein, said health drink obtained by combination of extract from plants Andrographis and Tinospora is superior to the one obtained from the plant Tinospora or Andrographis alone.

In still another embodiment of the present invention wherein, has extract of plants Andrographis and Tinospora in the ratio ranging between 25:1 to 1:150.

In still another embodiment of the present invention wherein, plant parts are crushed in water in ratio ranging between 1:1 to 1:1.5 to prepare aqueous extract.

In still another embodiment of the present invention, the aqueous extract can be prepared in both hot and cold water.

In still another embodiment of the present invention wherein, fermentation enhancer is mixed with the fruit base material at the concentration ranging between 10 to 20%.

In still another embodiment of the present invention wherein, said drink can be freshly prepared throughout the year.

In still another embodiment of the present invention wherein, plant extract is mixed with the fruit base material at the concentration ranging between 0.5 to 2%.

In still another embodiment of the present invention wherein, sugar is added to fruit filtrate in the ratio ranging between 1:3 and 2:5.

In still another embodiment of the present invention wherein, carbonated water is added to stock herbal drink in the ratio ranging between 1:3 to 2:5 to get herbal drink.

In still another embodiment of the present invention wherein, said drink has bitterness value ranging between 175 to 210.

In still another embodiment of the present invention wherein, all the vegetative part of the said plants contributes to bitterness.

In still another embodiment of the present invention wherein, said drink has alcohol content ranging between 2 to 8%.

In still another embodiment of the present invention wherein, said drink has aroma.

In still another embodiment of the present invention wherein, said drink claimed has refreshing property.

In still another embodiment of the present invention wherein, said drink claimed has an ability to quench thirst.

In still another embodiment of the present invention wherein, said drink provides instant energy.

In still another embodiment of the present invention wherein, said drink fight fatigue.

In still another embodiment of the present invention wherein, said drink is a safe health protective and preventive drink.

In still another embodiment of the present invention wherein, medicinal properties of said plant extract is not affected by the presence of other constituents of the said drink.

In an embodiment of the present invention, fermented health drink as herbal beer without hops, having characteristic bitter taste of beer, useful as an antioxidant, cardiotonic, diuretic, digestive, choleretic, nervine relaxant and immunomodulant, comprising extract from plant Andrographis with concentration ranging between 0.5 to 10%, extract from fruit, and ethanol ranging between 3 to 13% in the total health drink, optionally extract from plant Tinospora and other additives.

In still another embodiment of the present invention, for preparing herbal beer additives are selected from a group comprising coloring agents, sugar, carbonated water, and preservatives.

In still another embodiment of the present invention for preparing herbal beer has bitterness value ranging between 175 to 210.

In still another embodiment of the present invention wherein, for preparing herbal beer all the vegetative part of the said plants contributes to bitterness.

In still another embodiment of the present invention for preparing herbal beer has alcohol content ranging between 3 to 13%.

In still another embodiment of the present invention for preparing herbal beer wherein, said drink obtained by combination of extract from plants Andrographis and Tinospora is superior to the one obtained from the plant Tinospora or Andrographis alone.

In still another embodiment of the present invention for preparing herbal beer has extract of plants Andrographis and Tinospora in the ratio ranging between 25:1 to 1:150.

In still another embodiment of the present invention for preparing herbal beer can be freshly prepared throughout the year.

In still another embodiment of the present invention for preparing herbal beer wherein, plant extract is mixed with the fruit base material at concentration ranging between 0.5 to 2%.

In still another embodiment of the present invention for preparing herbal beer wherein, sugar is added to fruit base material in the ratio ranging between 1:3 and 2:5.

In still another embodiment of the present invention for preparing herbal beer wherein, carbonated water is added to stock herbal drink in the ratio ranging between 1:3 to 2:5 to get herbal drink.

In still another embodiment of the present invention herbal beer has aroma.

In still another embodiment of the present invention herbal beer has refreshing property.

In still another embodiment of the present invention herbal beer has an ability to quench thirst.

In still another embodiment of the present invention herbal beer provides instant energy.

In still another embodiment of the present invention herbal beer helps fight fatigue.

In still another embodiment of the present invention herbal beer is a safe health protective and preventive drink.

In an embodiment of the present invention a method of introducing bitterness into drink and using the said drink as herbal beer, said beer not containing hops and still retaining its characteristic bitter taste and also contributing to medicinal properties, comprising extract from plant Andrographis with concentration ranging between 0.5 to 10%, extract from fruit, and ethanol ranging between 3 to 13%, optionally extract from plant Tinospora and other additives.

In another embodiment of the present invention obtaining aqueous extract from said plant, In yet another embodiment of the present invention concentrating the aqueous extract, In still another embodiment of the present invention lyophilizing the concentrated extract, In still another embodiment of the present invention crushing optional fruit extract, In still another embodiment of the present invention mixing lyophilized extract with sugar, In still another embodiment of the present invention adding mixture of step (v) with said inoculum for fermentation, in aseptic conditions, In still another embodiment of the present invention fermenting mixture of step (vi) for 4 to 10 days, In still another embodiment of the present invention filtering the fermented material, In still another embodiment of the present invention pasteurizing the filtrate, In still another embodiment of the present invention obtaining stock herbal drink, In still another embodiment of the present invention adding carbonated water to stock herbal drink, and In still another embodiment of the present invention obtaining herbal beer.

In still another embodiment of the present invention additives are selected from a group comprising coloring agents, and preservatives.

In still another embodiment of the present invention wherein, said health drink obtained by combination of extract from plants Andrographis and Tinospora is superior to the one obtained from the plant Tinospora or Andrographis alone.

In still another embodiment of the present invention wherein, said drink is an antioxidant, cardio-tonic, diuretic, digestive, choleretic, nervine relaxant and immunomodulant.

In still another embodiment of the present invention wherein, extract of plants Andrographis and Tinospora in the ratio ranging between 25:1 to 1:150.

A method of producing health drink as claimed in claim 62 wherein, plant parts are crushed in water in ratio ranging between 1:1 to 1:1.5 to prepare aqueous extract.

In still another embodiment of the present invention, the said aqueous extract can be prepared by adding both cold and hot water in the plant material.

In still another embodiment of the present invention wherein, said drink can be freshly prepared throughout the year.

In still another embodiment of the present invention wherein, concentration of plant extract ranging between 0.5 to 2%.

In still another embodiment of the present invention wherein, sugar is added to the mixture in the ratio ranging between 1:3 and 2:5.

In still another embodiment of the present invention wherein, carbonated water is added to stock herbal drink in the ratio ranging between 1:3 to 2:5 to get herbal drink.

In still another embodiment of the present invention wherein, said drink has bitterness value ranging between 175 to 210.

In still another embodiment of the present invention wherein, all the vegetative part of the said plants contributes to bitterness.

In still another embodiment of the present invention wherein, said drink has alcohol content ranging between 3 to 13%.

In still another embodiment of the present invention wherein, said drink has aroma.

In still another embodiment of the present invention wherein, said drink claimed has refreshing property.

In still another embodiment of the present invention wherein, said drink claimed has an ability to quench thirst.

In still another embodiment of the present invention wherein, said drink provides instant energy.

In still another embodiment of the present invention wherein, said drink fight fatigue.

In still another embodiment of the present invention wherein, said drink is a safe health protective and preventive drink.

In still another embodiment of the present invention wherein, medicinal properties of said plant extract is not affected by the presence of other constituents of the said drink.

In still another embodiment of the present invention, advantage of using said plants in health drink is that, it is available throughout the year in tropical zones too and the vegetative parts like leaf and stem have all the aforesaid medicinal properties.

In still another embodiment of the present invention, the vegetative parts of selected plants may give bitterness to the drink.

In still another embodiment of the present invention, the part of medicinal herbs is selected from leaf, stem, root and whole plant.

In still another embodiment of the present invention, the selected plant parts are crushed in water in the ratio ranging between 1:1 to 1:1.5, to get the plant juices.

In still another embodiment of the present invention, a process for the preparation of plant extract the three layers of the Aqueous plant extract are separated out.

In still another embodiment of the present invention, the aqueous layer is concentrated by using rotavapor at a temperature of 50° C.

In still another embodiment of the present invention, all the three layers are lyophilized to make the powder form of the same.

In still another embodiment of the present invention, the raw fruits for preparing fruit based health drink are pealed off.

In still another embodiment of the present invention, the said pealed fruits and medicinal herb are crushed separately at room temperature.

In still another embodiment of the present invention, the crushed medicinal plant is mixed with the water in a ratio in the range of 1:3 to 2:7.

In still another embodiment of the present invention, the crushed fruits and aqueous mixture of medicinal herbs are filtered through muslin cloth separately.

In still another embodiment of the present invention, bitter powder from the plant extract is prepared.

In still another embodiment of the present invention, the base material from the crushed fruit is prepared.

In still another embodiment of the present invention, base material is autoclaved at 15 lbs. pressure for 15 to 20 minutes.

In still another embodiment of the present invention, said mixture is kept for fermentation for 4 to 10 days, in laboratory and 30–48 hrs. in frequenters.

In still another embodiment of the present invention, the said fermented material is filtered through muslin cloth.

In still another embodiment of the present invention, said filtrate is centrifuged at 10000 rpm for 15–30 minutes.

In still another embodiment of the present invention, the said filtrate as stock herbal drink is pasteurized.

In still another embodiment of the present invention, the said cereal grains are crushed and boiled or powdered.

In still another embodiment of the present invention, the combination of plant extract from Andrographis and Tinospora has better anti-oxidant, immunomodulation, hepatoprotectant, diuretic, nervine relaxant, anti-fatigue, digestive, cholerectic properties.

In an embodiment of the present invention, herbal beer from the combination of plants Andrographis and Tinospora is of superior quality as compared to the one formed from the plant Andrographis alone.

In still another embodiment of the present invention, herbal beer with none of the disadvantages of the conventional beer is developed.

In still another embodiment of the present invention, herbal beer with characteristic bitter taste of a conventional beer is developed.

In still another embodiment of the present invention beer with medicinal properties, such as antioxidant, anti-fatigue, health protective, immunomodulatory, hepatoprotective, diuretic etc, is developed.

In still another embodiment of the present invention, raw mango is optionally used as a base material to develop fruit based herbal beer with all the desired characteristics of the plant Andrographis alone and in combination with Tinospora.

In still another embodiment of the present invention, the combination of plant extract from Andrographis and Tinospora has better anti-oxidant, immunomodulation, hepatoprotectant, diuretic, nervine relaxant, anti-fatigue, digestive, cholerectic properties.

In an embodiment of the present invention a fermented herbal health drink useful as an antioxidant, cardio-tonic, diuretic, digestive, choleretic, nervine relaxant and immunomodulant, comprising extract from plant Andrographis with concentration ranging between 0.5 to 10%, extract from barley and/or wheat, and ethanol ranging between 3 to 13% in the total herbal health drink, optionally extract from plant Tinospora and other additives.

In another embodiment of the present invention a method of producing fermented herbal health drink useful as an antioxidant, cardio-tonic, diuretic, digestive, choleretic, nervine relaxant and immunomodulant, comprising extract from plant Andrographis with concentration ranging between 0.5 to 10%, extract from barley and/or wheat, and ethanol ranging between 3 to 13% in total health drink, optionally extract from plant Tinospora and other additives.

In yet another embodiment of the present invention obtaining aqueous extract from plant Andrographis, In still another embodiment of the present invention concentrating the aqueous extract, In still another embodiment of the present invention lyophilizing the concentrated extract, In still another embodiment of the present invention adding sugar to wheat and/or barley extract to form base material, In still another embodiment of the present invention autoclaving the said base material, In still another embodiment of the present invention mixing fermentation enhancer and lyophilized extract with base material, In still another embodiment of the present invention adding mixture of step (vii) with said inoculum for fermentation, in aseptic conditions, In still another embodiment of the present invention fermenting mixture of step (viii) for 4 to 10 days, In still another embodiment of the present invention filtering the fermented material, In still another embodiment of the present invention pasteurizing the filtrate, In still another embodiment of the present invention adding carbonated water to pasteurized filtrate, In still another embodiment of the present invention obtaining fermented health drink, and In still another embodiment of the present invention adding preservatives and coloring agents to drink of step (xiii).

In still another embodiment of the present invention, a local survey of about 100 people suggest that the herbal drink of instant application is liked by the bear drinkers and they feel that the herbal drink prepared by inventors can replace the conventional beer. The said herbal drink is liked for its special bitter tinge and medicinal properties. The data-sheet of the said survey is enclosed herewith.

In still another embodiment of the present invention, the bitterness value of different samples of a drink was determined according to the method given in "Quality control methods for medicinal plants"a WHO (1998) publication. However, it was determined using chloroquine phosphate as the positive control instead of quinine hydrochloride. Bitterness value of herbal drink in different batches ranged from 180 to 207.

| Herbal drink batches | Bitterness value |
|---|---|
| 1-With Andrographis extract (barley base) | 180.44 |
| 2-With Tinospora Extract + Andrographis extract (Mango base) | 193.33 |
| 3-With Andrographis extract only (Mango base) | 206.22 |
| 4-With Tinospora extract (Barely base) | 200.62 |
| It was also determined in market beer available commercially. | |
| Haywards 5000 | 189.03 |

In still another embodiment of the present invention the alcohol percentage indifferent samples of the drinks was determined according to the specific gravity method for alcohol (by volume) in beer given in the Official Methods of Analysis AOAC (fourth edition, 1984). In ranged from 2% to 8% in the same batches of herbal drink.

| Herbal drink batches | Alcohol percentage |
| --- | --- |
| 1-With Andrographis extract (barley base) | 2.75% |
| 2-With Tinospora Extract + Andrographis extract (Mango base) | 6.45% |
| 3-With Andrographis extract only (Mango base) | 5.71% |
| 4-With Tinospora extract (Barely base) | 2.48% |
| It was also determined in market beer available commercially. Haywards | 6.68% |

01QBAA650

019113750

The medicinal plants used in the fermented herbal drink are reported to have antioxidant, immunomodulator, anti-fatigue and hepatoprotective properties. No commercial beer has the aforesaid properties.

The following examples are provided to illustrate the invention in accordance with the principles of this invention, but are not to be construed as limiting the invention in any way

EXAMPLE 1

Mix 2.5 kg of barley malt, 750 g of sugar with 2.5 liters of distilled water. Add 40 g of lower layer of Andrographis spp. extract 25 g of yeast and keep the material in a fermenter for 48 hrs at a temperature of 30° C. After complete fermentation, filter the mixture and pasteurize, centrifuge at 12,000 rpm for 15 minutes. Prepare the drink by adding 25 ml of soda water to 15 ml of the prepared beer. Add preservatives in the concentration ranging between 2 to 10%. Add tartrazine as coloring agent.

EXAMPLE 2

Mix 2.0 kg of crushed and boiled wheat, 0.5 kg of sugar with 2 liters of distilled water. Add 25 g of lower layer, 5 g of middle layer of Andrographis aqueous extract and 25 g of yeast and keep the material in a fermenter for 48 hrs at a temperature of 30° C. After complete fermentation, filter the mixture and pasteurize. Centrifuge at 12,000 rpm for 15 minutes. Prepare the drink by adding 25 ml of soda water to 15 ml of the prepared beer. Add preservatives in the ratio ranging between 1 to 13%. Add caramel as coloring agent.

EXAMPLE 3

Mix 10 kg of barley malt extract, 4.0 kg of sugar, 150 g of Tinospora aqueous extract 2 g of Andrographis aqueous extract and 70 ml of Sacromysis strain (inoculum) with 15 liters of distill water keep the material in a fermenter for 40 hrs at a temperature of 30° C. After complete fermentation, filter the mixture and pasteurize, then centrifuge at 12,000 rpm for 30 minutes. Prepare the drink by adding 25 ml of soda water to 15 ml of the prepared beer. Add preservatives in the ratio ranging between 0.5 to 7%. Add $SO_2$ as a preservative.

EXAMPLE 4

Mix 2.4 kg of Mango pulp with 2.0 kg of sugar. Add 2.5 liters of distilled water then autoclave the mixture. Add 40 g of lower layer of andrographis spp. extract, 25 g of yeast (inoculum) and 0.5 kg of barley. Keep the material in a fermenter for 36 to 98 hrs. After fermentation, filter the mixture and pasteurize, centrifuge at 12,000 rpm for 15 minutes. Prepare the drink by adding 25 ml of soda water to 15 ml of the golden coloured stock solution and a pinch of salt. Add preservatives in the ratio ranging between 1 to 15%.

EXAMPLE 5

Mix 2.4 kg of Mango pulp with 2.5 kg of sugar and 2.5 liters of distill water. Autoclave the mixture. Add 175 g of aqueous extract of Tinospora to 25 g of dries aqueous extract of Andrographis spp. Sacromyces strain and 0.5 kg of crushed wheat, keep the mixture for 5 days for fermentation at a temperature of 30° C. Then the beer is filtered and pasteurized. To get the transparent golden color the beer is centrifuged at 10,000 rpm for 30 minutes.

To prepared a drink, 10 ml of stock herbal drink is further diluted with 25 ml of soda water. Add preservatives. Add tert-butyl hydroquinine as an anti-oxidant.

EXAMPLE 6

Mix 20 litres of Mango juice with 6.4 kg of sugar. Add 20 liters of distilled water and autoclave the mixture. Add 2 g of dried extract of Andrographis, 100 ml of Sacromyces inoculums and 1.6 kg of barley. Keep the material in a fermenter for 36 hrs. After completing fermentation, filter the mixture and pasteurize, then centrifuge at 12,000 rpm for 15 minutes. Prepare the drink by adding 25 ml of soda water to 15 ml of the golden coloured stock solution and a pinch of salt. Add preservatives in the ratio ranging between 4 to 20%.

EXAMPLE 7

Mix 2 litres of *Phyllanthus emblica* fruit juice with 1 kg of sugar then add 2 liters of distill water, autoclave the mixture for 30mins at 15 pound. Add 20 g each of middle and lower layers of Andrographis extract and 100 g of yeast. The mixture kept for fermentation for 5 days, filter and centrifuge at 12,000 rpm for 45mins and then autoclaved. 10 ml of this stock herbal beer is further diluted with 25 ml of soda water and ready for use. And if desired add preservatives.

EXAMPLE 8

Mix 3 liters of water melon juice, 1.5 liters of pomegranate juice and 405 g of sugar then add 25 g of aqueous extract of Andrographis and autoclave the mixture. Then add 20 ml of Sacromyces strain. Filter the material after 4 days complete fermentation, centrifuge at 12,000 rpm for 30 minutes and then autoclave for 15 minutes. Add 20 ml of said water to 10 ml of the above stock herbal beer and add a small pinch of salt. Add preservatives.

What is claimed is:

1. A fermented fruit based herbal health drink composition useful as an antioxidant, cardio-tonic, diuretic, digestive, choleretic, nervine relaxant and immunomodulant, comprising extract from plant Andrographis with concentration ranging between 0.5 to 10% in the total herbal health drink, extract from fruit, and ethanol ranging between 3 to 13% in the total herbal health drink, optionally extract from plant Tinospora and other additives.

2. The health drink as claimed in claim 1 wherein, other additives are selected from a group consisting of coloring agents, sugar, carbonated water and preservatives.

3. The health drink as claimed in claim 1 wherein, the drink further comprises fermentation enhancers which are selected from a group consisting of grains of wheat and barley.

4. The health drink as claimed in claim 1 wherein, fruits are selected from a group consisting of *Mangifera indica, Phyllanthus emblica, Psidium guajava*, and *Citrus* spp.

5. The health drink as claimed in claim 1, wherein said extract of plants Andrographis and Tinospora are in the ratio ranging between 25:1 to 1:150.

6. The health drink as claimed in claim 1 wherein, Andrographis plant material is crushed in water in a ratio ranging between 1:1 to 1:1.5.

7. The health drink as claimed in claim 3 wherein, the fermentation enhancer is mixed with the fruit extract at the concentration ranging between 10 to 20%.

8. The health drink as claimed in claim 1 wherein, Andrographis plant extract at concentration ranging between 0.5 to 2% is mixed with fruit extract.

9. The health drink as claimed in claim 1 wherein, sugar is added to fruit extract in the ratio ranging between 1:3 and 2:5.

10. The health drink as claimed in claim 1 wherein, carbonated water is added to a concentrate of the herbal drink in a ratio ranging between 1:3 to 2:5.

11. The health drink as claimed in claim 1 has bitterness value ranging between 175 to 210.

12. The health drink as claimed in claim 1 wherein, all the vegetative part of the said plants contribute to bitterness.

13. The health drink as claimed in claim 1 has an alcohol content ranging between 2 to 8%.

14. The health drink claimed in claim 1 wherein said drink has aroma, refreshing property, an ability to quench thirst, provides instant energy, fight fatigue, safe, health protective.

15. The health drink claimed in claim 1 wherein, medicinal properties of said Andrographis plant extract are not affected by the presence of other constituents of the drink.

16. A method of producing a fermented fruit based herbal health drink composition useful as an antioxidant, cardiotonic, diuretic, digestive, choleretic, nervine relaxant and immunomodulant, comprising extract from plant Andrographis with a concentration ranging between 0.5 to 10% based on the total health drink, extract from fruit, and ethanol ranging between 3 to 13% in total health drink, optionally extract from plant Tinospora, said method comprising:
   (i) obtaining aqueous extract from plant Andrgruphis and optionally Tinospora,
   (ii) concentrating the aqueous extract,
   (iii) lyophilizing the concentrated extract,
   (iv) adding sugar to fruit extract,
   (v) obtaining fruit base material,
   (vi) autoclaving said base material,
   (vii) mixing fermentation enhancer and lyophilized extract with base material,
   (viii) adding the mixture of step (vii) with an inoculum for fermentation, in aseptic conditions,
   (ix) fermenting mixture of step (viii) for 4 to 10 days,
   (x) filtering the fermented material and obtaining a fruit filtrate,
   (xi) pasteurizing the filtrate,
   (xii) adding carbonated water to the pasteurized filtrate,
   (xiii) obtaining a fermented fruit based health drink, and
   (xiv) adding preservatives and coloring agents to the drink of step (xiii).

17. A method as claimed in claim 16 wherein, other additives are selected from a group consisting of coloring agents, sugar, carbonated water, preservatives and coloring agents.

18. A method as claimed in claim 16 wherein, fermentation enhancers selected from a group consisting of grains of wheat and barley are further added to the drink.

19. A method as claimed in claim 16 wherein, fruits are selected from a group consisting of *Mangifera indica, Phyllanthus emblica, Psidium guajava*, and *Citrus* spp.

20. A method as claimed in claim 16 wherein, said extract of plants Andrographis and Tinospora are in the ratio ranging between 25:1 to 1:150.

21. A method of producing health drink as claimed in claim 16 wherein, Andrographis plant parts are crushed in water in a ratio ranging between 1:1 to 1:1.5.

22. A method as claimed in claim 16 wherein, the fermentation enhancer is mixed with the fruit base material at the concentration ranging between 10 to 20%.

23. A method as claimed in claim 16 wherein, said drink can be freshly prepared throughout the year.

24. A method as claimed in claim 16 wherein, Andrographis plant extract at a concentration ranging between 0.5 to 2% based on the whole drink composition is mixed with the fruit base material.

25. A method as claimed in claim 16 wherein, sugar is added to fruit filtrate in the ratio ranging between 1:3 and 2:5.

26. A method as claimed in claim 16, wherein carbonated water is added to a concentrate of the herbal drink in the ratio ranging between 1:3 to 2:5 to get an herbal drink.

27. A method as claimed in claim 16 wherein, said drink has bitterness value ranging between 175 to 210.

28. A method as claimed in claim 16 wherein, all the vegetative part of the said plants contributes to bitterness.

29. A method as claimed in claim 16 wherein, said drink has alcohol content ranging between 2 to 8%.

30. A method as claimed in claim 16 wherein, said drink has aroma, refreshing property, an ability to quench thirst, provides instant energy, fight fatigue, safe, and health protective.

31. A method as claimed in claim 16 wherein, medicinal properties of said Andrographis plant extract are not affected by the presence of other constituents of the drink.

32. A fermented herbal health drink composition useful as an antioxidant, cardio-tonic, diuretic, digestive, choleretic, nervine relaxant and immunomodulant, comprising extract from plant Andrographis with a concentration ranging between 0.5 to 10% based on the total drink, extract from barley and/or wheat, and ethanol ranging between 3 to 13% in the total herbal health drink, optionally extract from plant Tinospora and other additives.

33. The health drink as herbal beer without hops as claimed in claim 32 wherein, other additives are selected from a group consisting of coloring agents, sugar, carbonated water, and preservatives.

34. The health drink as herbal without hops as claimed in claim 32 wherein, fruits are selected from a group consisting of *Magifera indica, Phyllanthus emblica, Psidium guajava*, and *Citrus* sup.

35. The health drink as herbal beer without hops as claimed in claim 32 has bitterness value ranging between 175 to 210.

36. The health drink as herbal beer without hops as claimed in claim 32 wherein, all the vegetative part of the said plants contributes to bitterness.

37. The health drink as herbal beer without hops as claimed in claim 32, which has an alcohol content ranging between 2 to 8%.

38. The health drink as herbal beer without hops as claimed in claim 32, wherein said extract of plants Andrographis and Tinospora are in the ratio ranging between 25:1 to 1:150.

39. The health drink as claimed in claim 32, wherein Andrographis plant material is crushed in water in a ratio ranging between 1:1 to 1:1.5.

40. The health drink as herbal beer without hops as claimed in claim 32 wherein, Andrographis plant extract at a concentration ranging between 0.5 to 2%, based on the total drink is mixed with the fruit extract.

41. The health drink as herbal beer without hops as claimed in claim 32 wherein, sugar is added to fruit extract in the ratio ranging between 1:3 and 2:5.

42. The health drink as herbal beer without hops as claimed in claim 32 wherein, carbonated water is added to a concentrate of the herbal drink in a ratio ranging between 1:3 to 2:5 to get an herbal drink.

43. The health drink as herbal beer without hops as claimed in claim 32 has aroma, refreshing property, an ability to quench thirst, provides instant energy, helps fight fatigue, safe, and health protective.

44. A method of introducing bitterness into a drink composition and using the said drink as herbal beer, said beer not containing hops and still retaining a bitter taste and also contributing to medicinal properties, comprising extract from plant Andrographis with a concentration ranging between 0.5 to 10% based on the total drink, extract from fruit, and ethanol ranging between 3 to 13% in the total herbal health drink, optionally extract from plant Tinospora, said method comprising:

(i) obtaining aqueous extract from plant Andrographis and optionally Tinospora, (ii) concentrating the aqueous extract, (iii) lyophilizing the concentrated extract, (iv) crushing fruit pulp to get fruit extract, (v) mixing lyophilized extract with sugar and fruit extract, (vi) adding mixture of step (v) with an inoculum for fermentation, in aseptic conditions, (vii) fermenting mixture of step (vi) for 4 to 10 days, (viii) filtering the fermented material, (ix) pasteurizing the filtrate, (x) obtaining concentrate herbal drink, (xi) adding carbonated water to concentrate herbal drink, and (xii) obtaining herbal beer.

45. A method as claimed in claim 44 wherein, additives are selected from a group consisting of coloring agents, sugar, carbonated water and preservatives.

46. A method as claimed in claim 44 wherein, fruits are selected from a group consisting of *Mangifera indica, Phyllanthus emblica, Psidium guajava,* and *Citrus* spp.

47. A method as claimed in claim 44 wherein, said drink is an antioxidant, cardio-tonic, diuretic, digestive, choleretic, nervine relaxant and immunomodulant.

48. A method as claimed in claim 44 wherein, said extract of plants Andrographis and Tinospora are in the ratio ranging between 25:1 to 1:150.

49. A method as claimed in claim 44 wherein, Andropgraphis plant parts are crushed in water in a ratio ranging between 1:1 to 1:1.5.

50. A method as claimed in claim 44 wherein, said drink can be freshly prepared throughout the year.

51. A method as claimed in claim 44 wherein, concentration of Andropgraphis plant extract is between 0.5 to 2% based on the total drink composition.

52. A method as claimed in claim 44 wherein, sugar is added to the mixture in the ratio ranging between 1:3 and 2:5.

53. A method as claimed in claim 44 wherein, carbonated water is added to stock herbal drink in the ratio ranging between 1:3 to 2:5 to get herbal drink.

54. A method as claimed in claim 44 wherein, said drink has bitterness value ranging between 175 to 210.

55. A method as claimed in claim 44 wherein, all the vegetative part of the said plants contributes to bitterness.

56. A method as claimed in claim 44 wherein, said drink has alcohol content ranging between 3 to 13%.

57. A method as claimed in claim 44 wherein, said drink has aroma, has refreshing property, an ability to quench thirst, provides instant energy, fight fatigue, safe, and health protective.

58. A method as claimed in claim 44 wherein, medicinal properties of said Andropgraphis plant extract are not affected by the presence of other constituents in the drink.

59. A fermented herbal health drink composition useful as an antioxidant, cardio-tonic, diuretic, digestive, choleretic, nervine relaxant and immunomodulant, comprising extract from plant Andrographis with a concentration ranging between 0.5 to 10% based on the total drink, extract from barley and/or wheat, and ethanol ranging between 3 to 13% in the total herbal health drink, optionally extract from plant Tinospora and other additives.

60. The health drink as claimed in claim 59 wherein, other additives are selected from a group consisting of coloring agents, sugar, carbonated water and preservatives.

61. The health drink as claimed in claim 59 wherein said extract of plants Andrographis and Tinospora are in a ratio ranging between 25:1 to 1:150.

62. The health drink as claimed in claim 59 wherein, Andrographis plant material is crushed in water in a ratio ranging between 1:1 to 1:1.5.

63. The health drink as claimed in claim 59 can be freshly prepared throughout the year.

64. The health drink as claimed in claim 59 wherein, carbonated water is added to stock herbal drink in the ratio ranging between 1:3 to 2:5 to get herbal drink.

65. The health drink as claimed in claim 59 has bitterness value ranging between 175 to 210.

66. The health drink as claimed in claim 59 wherein, all the vegetative part of the said plants contribute to bitterness.

67. The health drink as claimed in claim 59, which has an alcohol content ranging between 2 to 8%.

68. The health drink claimed in claim 59 wherein said drink has aroma, refreshing property, an ability to quench thirst, provides instant energy, fight fatigue, safe, health protective.

69. The health drink claimed in claim 59 wherein, medicinal properties of said Andrographis plant extract are not affected by the presence of other constituents of the drink.

* * * * *